(12) United States Patent
Nagane et al.

(10) Patent No.: US 6,444,640 B1
(45) Date of Patent: Sep. 3, 2002

(54) COMPOSITIONS OF TRAIL AND DNA DAMAGING DRUGS AND USES THEREOF

(75) Inventors: Motoo Nagane; Webster Cavenee; Su Huang, all of La Jolla, CA (US)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/409,336

(22) Filed: Sep. 30, 1999

(51) Int. Cl.7 .............................................. A61K 38/00
(52) U.S. Cl. ......................................................... 514/2
(58) Field of Search ............................................. 514/2

(56) References Cited

U.S. PATENT DOCUMENTS 5,763,223 A * 6/1998 Wiley et al. ............... 435/69.5

* cited by examiner

*Primary Examiner*—Zohreh Fay
(74) *Attorney, Agent, or Firm*—Fulbright & Jaworski L.L.P.

(57) ABSTRACT

The invention relates to compositions which include both a DR5 binding ligand, such as TRAIL, and a DNA damaging agent. In combination, these two materials have unexpected efficacy in treating conditions involving rapid cellular turnover, such as cancer, where an increase in apoptosis is desired. The compositions are particularly effective in treating neoplasias and diseases involving proliferative lesions, such as glioma.

9 Claims, 7 Drawing Sheets

COMPOSITIONS OF TRAIL AND DNA DAMAGING DRUGS AND USES THEREOF

FIELD OF THE INVENTION

This invention relates to compositions useful in treating patients afflicted with diseases involving rapid cellular turnover, such as cancer, and methods of treatment which utilize these compositions. More particularly, it relates to treatment of cancers such as glioblastomas.

BACKGROUND AND PRIOR ART

Malignant glioma is the most common primary brain tumor. Notwithstanding a number of intensive, multimodality treatments including surgical resection, irradiation and chemotherapy, gliomas are considered to be incurable. The 5 year survival rate of patients with glioblastoma multiforme, the most malignant form of glioma, is less than 10%. See, e.g., Dean, et al., J. Neuroncol 16: 243–272 (1993). Genetic analyses have defined a number of alterations which accumulate during the malignant progression of gliomas, including alterations in the TP53, CDKN2A, RB1, PTEN, EGFR, and MDM2 genes. See Nagane, et al., Curr. Opin. Oncol 9: 215–222 (1997), incorporated by reference on this issue. It also now seems to be the case that glioblastomas can be divided into two distinct genetic subsets, where p53 inactivation and amplification of EGFR are mutually exclusive genetic lesions. See Louis, et al., Trends Genet. 11: 412–415 (1995); Reifenberger, et al., J. Neuorpathol. Exp. Neural 55: 822–831 (1996); Watanabe, et al., Brain Pathol. 6: 217–223 (1996). About 40% of glioblastomas exhibit p53 mutations, and progress from lower grade lesions. Other glioblastomas with wild type p53 occur de novo, mostly in older patients, exhibit rapid clinical course, and are frequently associated with EGFR alterations. See Louis et al., supra; Reifenberger, et al., supra. There is some evidence that these, latter de novo type of glioblastoma may be more resistant to chemotherapy than other types (Mason, et al., J. Clin. Oncol 15: 3423–3426 (1997), and studies have shown that malignant gliomas in younger patients respond significantly better to chemotherapy than those in older patients. See Grant, et al., Neurol 45: 929–933 (1995).

In vitro studies have shown that astrocytes from p53 knockout mice are more sensitive to 1,3 bis (2-chloroethyl)-1-nitrosourea("BCNU" hereafter) than are wild type astrocytes. See Nutt, et al., Cancer Res 56: 2748–2751 (1996). Further, overexpression of mutant EGFR, which is common in de novo glioblastoma has been demonstrated to confer drug resistance in human glioblastoma cells which exhibit wild type p53. See Nagane, et al., Proc. Natl. Acad. Sci. USA 95: 5724–5729 (1998). Hence, clinically more aggressive, "de novo" glioblastoma remains a major obstacle for successful glioma therapy.

It is known that the p53 tumor suppressor protein is a major regulator of cell cycle arrest, DNA repair, and apoptosis that is induced upon DNA damage, and other forms of genotoxic stress. See Roley, et al., Important Adv. Onco 1996: 37–56 (1996). Since most de novo type glioblastomas retain wild type p53, one possible approach to treatment might be to activate and to utilize the apoptosis related functions of p53.

There are multiple pathways involved in p53 mediated apoptosis. Further, a family of so-called "death receptors", or "DRs" which contain cytoplasmic death domains have been found to be transcriptionally upregulated, in p53 dependent manner, by DNA damage, in some human cancer cells. See Muller, et al., J. Clin. Invest. 99: 403–413 (1997); Sherkh, et al., Cancer Res. 58: 1593–1598 (1998); Wu, et al., Nature Genet. 17: 141–143 (1997).

One such receptor, "DR5," also named "killer/TRAIL-R2" specifically binds to tumor necrosis factor related apoptosis inducing ligand, or "TRAIL." Information on "TRAIL" can be found in, e.g., U.S. Pat. No. 5,763,223, incorporated by reference. DR5, via binding to TRAIL, mediates TRAIL induced apoptosis via activation of effector caspases. See Wu, et al., supra; Wiley, et al., Immunity 3: 673–682 (1995); Pitti, et al., J. Biol. Chem 271: 12687–12690 (1996); Pan, et al., Science 277: 815–818 (1997); Sheridan, etal., Science 217: 818–821 (1997); Walczak, et al., EMBO J 16: 5386–5397 (1997). TRAIL also binds to another death receptor, "DR4," (Pan, et al., Science 276: 111–113 (1997)), which is another receptor that mediates apoptosis, as well as to two additional receptors, i.e., DcR1(TRID/TRAIL-R3), and DcR2 (TRUNDD/TRAIL-R4), both of which lack death domains. See Pan, et al., Science 277: 815–818 (1997); Sheridan, et al., Science 277: 818–821 (1997); Degli-Esposti, et al., J. Exp. Med. 186: 1165–1170 (1997); Degli-Esposti, et al., Immunity 7: 813–820 (1997); Marsters, et al., Curr. Biol 7: 1003–1006 (1997); Pan, et al., Febs Lett 424: 41–45 (1998).

In view of this information, it was of interest to determine if TRAIL, in combination with DNA damaging drugs, could be used to alleviate cancers, such as glioblastoma. How this is accomplished is the subject of the invention which is set forth in the disclosure which follows.

DETAILED DESCRIPTION OF PREFERRED EMBODIMENTS

EXAMPLE 1

Figure 1:
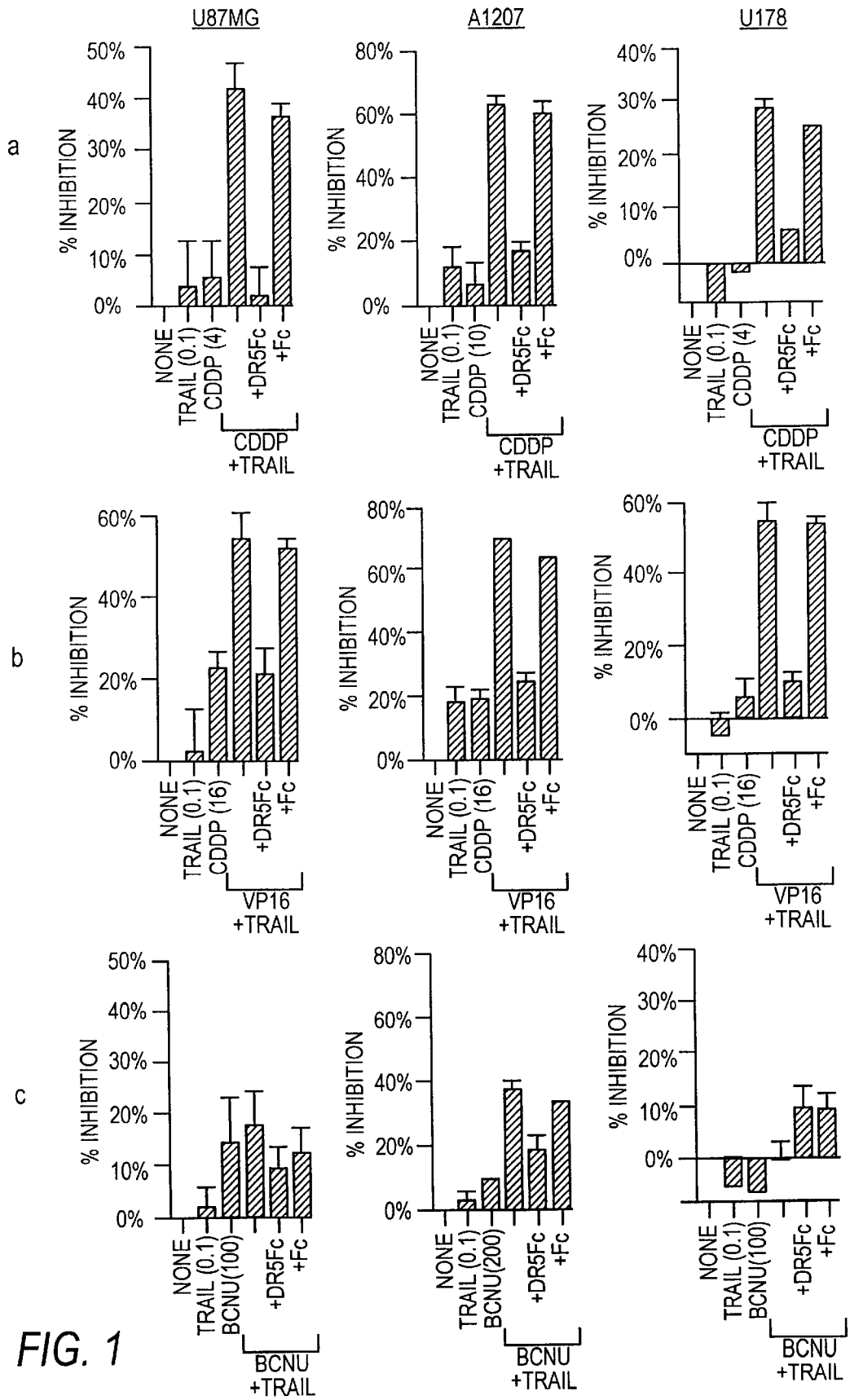
FIG. 1 shows synergistic effect of the compositions of the invention.

This first set of experiments was designed to determine whether chemotherapeutic agents which are used in treating gliomas could upregulate expression of DR5 in human glioma cell lines. This was apreliminary step to determine if wild type p53, which is found in de novo glioblastomas, could be exploited.

The human glioblastoma cell lines U87MG, A1207, and U178 were used. The first two of these cell lines are homozygous for wild type p53, while U178 cells express a wild type allele, and an allele with a mutation at codon 271. Samples of cells were treated with one of cis-diamminedichloroplatinum (II) ("CDDP" hereafter), ectoposide ("VP16" hereafter), or chloroethyl)-BCNU. The U87MG and U178 cells received either 0, 1, or 4 ug/ml doses of CDDP; 0, 8, or 16 ug/ml doses of VP16, or 0, 100, or 200 $\mu$M doses of BCNU. The A1207 cells received 0, 5, or 20 ug/ml of CDDP, 0, 8 or 16 ug/ml of VP16, or 0, 100, or 200 µM doses of BCNU.

The cells were treated with the drug at an indicated dosage for 16 hours, after which they were harvested, and total RNA was extracted, following standard methods. Then, 15 ug samples were size fractionated on a 1% agarose formaldehyde gel, and transferred to a nylon membrane. These samples were then probed with a human DR5 cDNA probe, 583 base pairs long. This had beenz prepared via RT-PCR of total RNA of U87MG cells using:

CTGAAAGGCA TCTGCTCAGG TG (SEQ ID NO: 1) and

CAGAGTCTGC ATTACCTTCT AG (SEQ ID NO: 2).

The hybridization was carried out at 68° C. for 2 hours, followed by washing in 0.5×SSC and 0.1% SDS at 58° C. for 15 minutes. The membranes were then exposed to film at −80° C. with an intensifying screen. In order to confirm that RNA had in fact been loaded, 28SrRNA was stained with methylene blue.

The results indicated that the basal level expression of ~4.4Kb DR5 transcripts increased significantly after contact with CDDP or VP16. Induction by these agents was dose, drug type, and time dependent. The induction by VP16 was apparent after two hours, while induction required 16 hours of contact with CDDP. BCNU had a lesser effect on DR5 expression.

EXAMPLE 2

In further experiments, the expression levels of other TRAIL receptors and of endogenous TRAIL itself was assayed, using specific probes for the cDNA in question (DcR1, DR4, DcR2, TRAIL, and DR5). cDNA encoding GAPDH was used as a loading control. Six ug total RNA was isolated both before and after treatment of the cells with CDDP (4 ug/ml for U87MG and U178, 10 ug/ml for A1207), or VP16 (16 ug/ml), and then subjected to an RNase protection assay, using a commercially available system.

DR5 levels increased, which is consistent with example 1, supra. DR4 was also upregulated in U87MG and A1207, but to a lesser extent than DR5. The expression of two TRAIL decoy receptors, DcR1 and DcR2, was only detectable at trace levels, and only in U87MG cells. TRAIL transcripts were completely undetectable.

EXAMPLE 3

The preceding examples showed that DR5 expression was enhanced upon exposure to DNA damaging agents. Experiments were then carried out to determine if combining TRAIL with the damaging agents would enhance cytotoxicity. The method employed to determine if combining TRAIL with the damaging agents would enhance cytotoxicity was the 3-(4,5-dimethylthiazol-2-yl)-2,5-diphenyl tetrazolum bromide ("MTT") survival assay, described by Mosmann, et al., J. Immunol. Meth 65: 55–63 (1983), incorporated by reference. Cells (U87MG) were plated, at 1×10$^4$ cells/well in 96 well microtiter plates overnight. They were then treated with 200 ul of fresh medium containing the drug under consideration (TRAIL: 0.1 ug/ml; CDDP: 4 ug/ml; VP16: 16 ug/ml; TRAIL (0.1 ug/ml) plus CDDP (4 ug/ml), or TRAIL (0. 1 ug/ml plus VP16 (16 ug/ml). When combinations of two drugs were used, the two were used alone, or with one of DR5-Fc, Fc, or caspase inhibitor Z-Asp-CH$_2$-DCB. The treatments continued for 24 hours, followed by 4 hours of contact with 250 ug/ml of MTT, followed by analysis. The results are set forth in FIG. 1.

The doses of the drugs (CDDP, VP16), used were sublethal but sufficient to induce DR5 expression. When combined with a low concentration of TRAIL that in and of itself had no effect on cell viability induced substantial cell death syngergistically, in accordance with Webb, *Effects of More Than One Inhibitor in Enzymes and Metabolic Inhibitors* Vol. 1 (Webb, ed.), pp. 487–512 (1963), incorporated by reference. Synergistic cytotoxicitywas abolishedby competition for TRAIL by DR5-Fc, a soluble fusion protein, but not by Fc alone.

It was also found that when the extracellular domain of DR4 was expressed as a fusion protein with Fc, the same elimination of synergistic cytotoxicity was observed, indicating that the effect is mediated by an event that occurs subsequent to TRAIL-receptor binding.

EXAMPLE 4

In these experiments, the mechanism by which the cell death caused by combination of TRAIL and DNA damaging agents was studied further. U87MG cells were plated overnight, and then treated with either TRAIL alone (0.1 ug/ml), CDDP alone (4 ug/ml) VP16 alone (16 ug/ml) TRAIL and CDDP, at the recited doses, or TRAIL plus VP16, at the recited doses. The cells were treated for 44 hours, collected, fixed in 2% formaldehyde, and permeabilized in 0.05% Tween-20 in bovine serum albumin solution.

The cells were then incubated with TUNEL (terminal deoxynucleotidyl transferase mediated nick end labeling) solution, at 37° C. for 1 hour. Those cells which stained positively with fluorescein were analyzed via flow cytometry. The morphology of the dead cells was typical of apoptosis.

EXAMPLE 5

The cytotoxic effect of TRAIL, in combination with one of the DNA damaging agents discussed supra, i.e., CDDP, VP16, as BCNU was tested, by either adding TRAIL alone, the drug alone, or TRAIL plus the drug, in a two component combination, with DR5-Fc, referred to supra, or with Fc. The dosages were as provided supra.

It was found that, when used in combination, the amount of TRAIL necessary for efficacy was about 100 fold less than what was necessary when it was used alone, and about half of the DNA damaging agent was necessary. FIG. 1, discussed supra, shows this.

EXAMPLE 6

Figure 2:
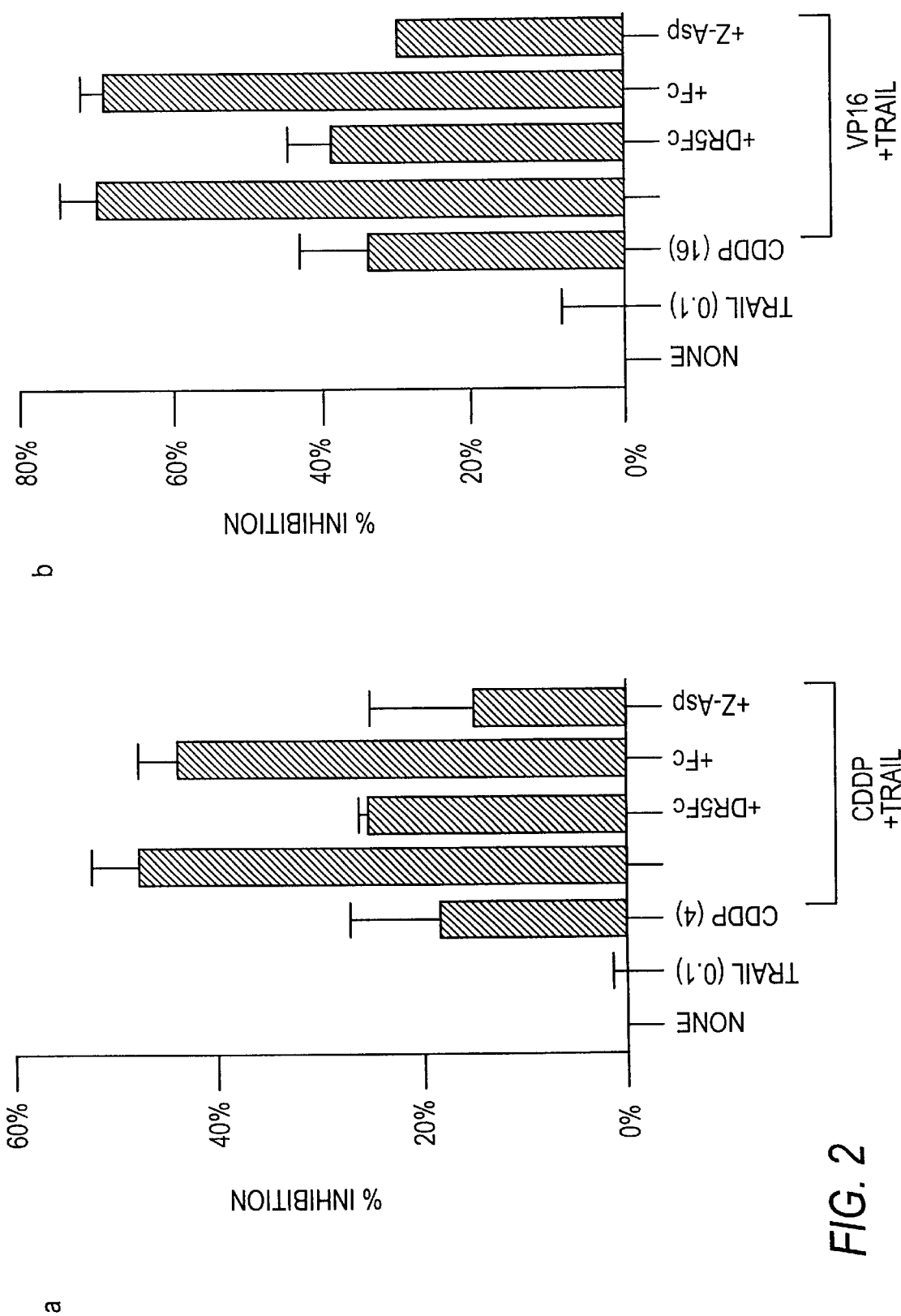
FIG. 2 shows the effect of caspase inhibitors on apoptosis induced by the compositions of the invention.

TRAIL is known to induce apoptosis through activation of effector caspases. See, e.g., Wu, et al., Nature Genet 17: 141–143 (1997); Wiley et al., Immunity 3: 673–682 (1995); Pitti, et al., J. Biol Chem 271: 12687–12690 (1996); Pan, et al., Science 277: 815–818 (1997); Sheridan, et al., Science 277: 818–821 (1997); Walczak, et al., EMBO J. 16: 5386–5397 (1997). Hence, experiments were designed to determine if caspase activation was involved in the synergistic cytotoxicity that was observed. In experiments reported supra, treatment of U87MG cells with TRAIL, one of CDDP or VP16, and the caspase inhibitor Z-Asp-CH$_2$-DCB, did not induce apoptosis. Further, cytotoxicity was observed to be at levels obtained for single drugs. See FIG. 2.

U87MG cells which overexpressed a cowpox virus derived caspase inhibitor, "CrmA," were prepared and tested as well. A viral CrmA expression vector was prepared by cotransfecting "293" kidney cells with a vector encoding CrmA, and a plasmid that encodes vesicular stomatitis virus G glycoprotein (See Yee, et al. Proc. Natl. Acad. Sci USA 91: 9564–9568 (1994)). Supernatant was harvested 3 days after transfection, and was condensed via centrifugation to obtain high titer retrovirus. An empty viral control, referred to as pBp, was also used.

The cells transfected with CrmA and thus overexpressing the caspase inhibitor did not respond to treatment with the combination drugs while the control did.

The direct assessment of activation of effector caspases was examined by assaying for cleavage of poly (ADP-ribase) polymerase, or "PARP", after treatment with combinations of a DNA damaging agent (CDDP or VP16), TRAIL, DR5-Fc or Fc, and the caspase inhibitor, Z-Asp-$CH_2$-DCB. This was determined via Western blotting, where 20 ug of clarified protein lysate was loaded onto SDS gels 24 hours after treatment, electrophoresed, transferred to membranes, and then probed with monoclonal antibodies against PARP. Full length PARP has a molecular weight of about 116 kilodalton and, when cleaved, one fragment is 85 kilodaltons.

It was found that the cleavage product was elicited when TRAIL and either CDDP or VP16 were used, but not when any one of these were used alone. The cleavage was inhibited when DR5-Fc or Z-ASP-$CH_2$-DCB were used.

Caspases can be activated by single therapeutic agents, so data were evaluated to determine if caspase activation was required to upregulate DR5. Minimal activation of effector caspases was observed when sublethal levels of DNA damaging drugs were used, as was evidenced by no obvious PARP cleavage. These same treatments resulted in clear increases of mRNA to DR5, as shown supra. The pattern was repeated for A1207 and U178 cells, suggesting that caspase activation is required for cell killing but not for DR5 upregulation.

EXAMPLE 7

The preceding examples demonstrate synergistic cytotoxicity in vitro. It was of interest to determine if the same effect would result in vivo.

To test this, U87MG cells ($2 \times 10^6$) were suspended in 0.1 ml PBS, and then injected subcutaneously into the right flank of 4–5 week old female nude mice, of BALB/C background. Tumors were permitted to become established, and then grow for 20 days, reaching an approximate innate volume of 150 $mm^3$. Then, either CDDP (3 mg/kg), or sterile normal saline was administered intraperitoneally on days 20,21,22,30,31, and 32. Mice also received either fusion protein FLAG-TRAIL (200 ug), or a mock control. The FLAG-TRAIL fusion protein described by Degli-Esposti, et al., J. Exp. Med 186: 1165–1170 (1997), incorporated by reference, was prepared via standard recombinant methods. Mock controls were prepared by carrying out the same protocol used to produce the FLAG-TRAIL, but without a vector which encoded the fusion protein. Cell lysate was used as the control. The FLAG-TRAIL or control was administered via intraveneous and intraperitoneal injections 16 hours and 24 hours following CDDP treatment, i.e., on days 21,22,23, 31,32 and 33. Growth of the tumors was measured at 2 day intervals, in accordance with Huang, et al., J. Biol Chem 272: 2972–2935 (1997).

No significant body weight loss or obvious neurological sequelae were observed in any of the treatment groups, nor were any appreciable changes observed in the liver, kidney, or brains of the mice when these organs were subjected to histological analysis, with the exception of minor, non-specific single cell necrosis in livers.

Figure 3:
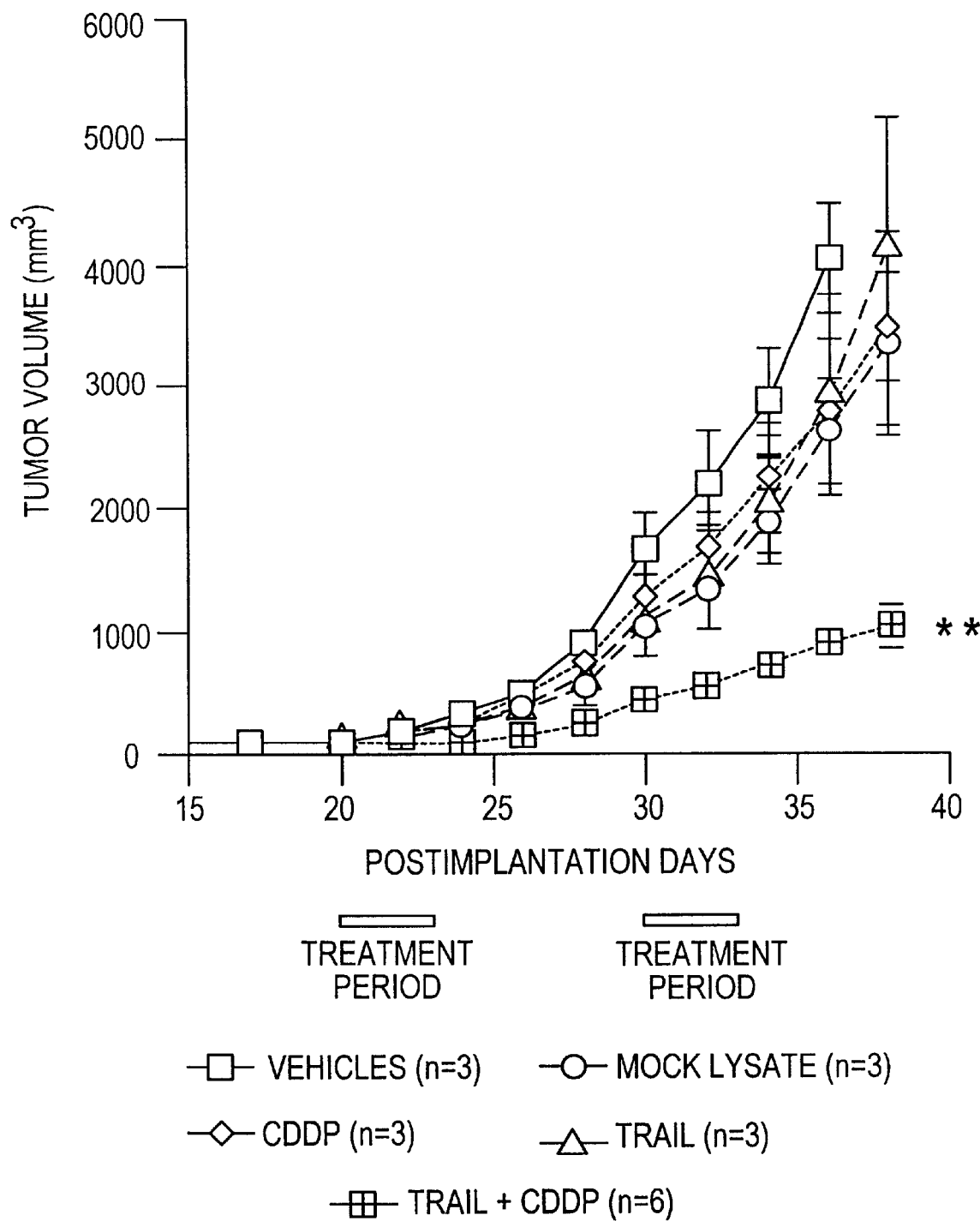
FIG. 3 depicts in vivo results obtained using the inventive compositions.

The tumors carried by the mice that had been treated with a combination of TRAIL (400 ug/day), and CDDP (3 mg/kg), did not grow for several days following the first course of treatment, and tumor growth was also suppressed by a second course of treatment. In contrast, animals which received mock control, or one of CDDP or TRAIL grew significantly faster than those treated with the combined drugs. Results are shown in FIG. 3.

EXAMPLE 8

These experiments compare TRAIL, CDDP, and combinations of the two drugs in the suppression of established, U87MG xenografts in nude mice.

A total of 21 mice were inoculated, subcutaneously, as described supra, with $2 \times 10^6$ U87MG cells, which were allowed to form established tumors. Thirteen days after the inoculation, tumors were established. Mice were then divided into four different treatment groups. The first group received only the drug vehicle (4 animals), a second group (4 animals) received 500 ug of TRAIL per day, in two doses (one intravenous, one intraperitoneal, each dose was 250 ug of TRAIL), for 3 days per week. The third group (4 animals), received 3 mg/kg of CDDP per day, intraperitoneally, for 4 days per week. The last group (9 animals), were dosed with both drugs. For the control, a combination of bacterial lysate and normal saline was used, to correspond to the drug combination.

The animals received six courses of treatment, and tumor volume (in $mm^3$) was measured throughout the treatment protocol.

Figure 4:
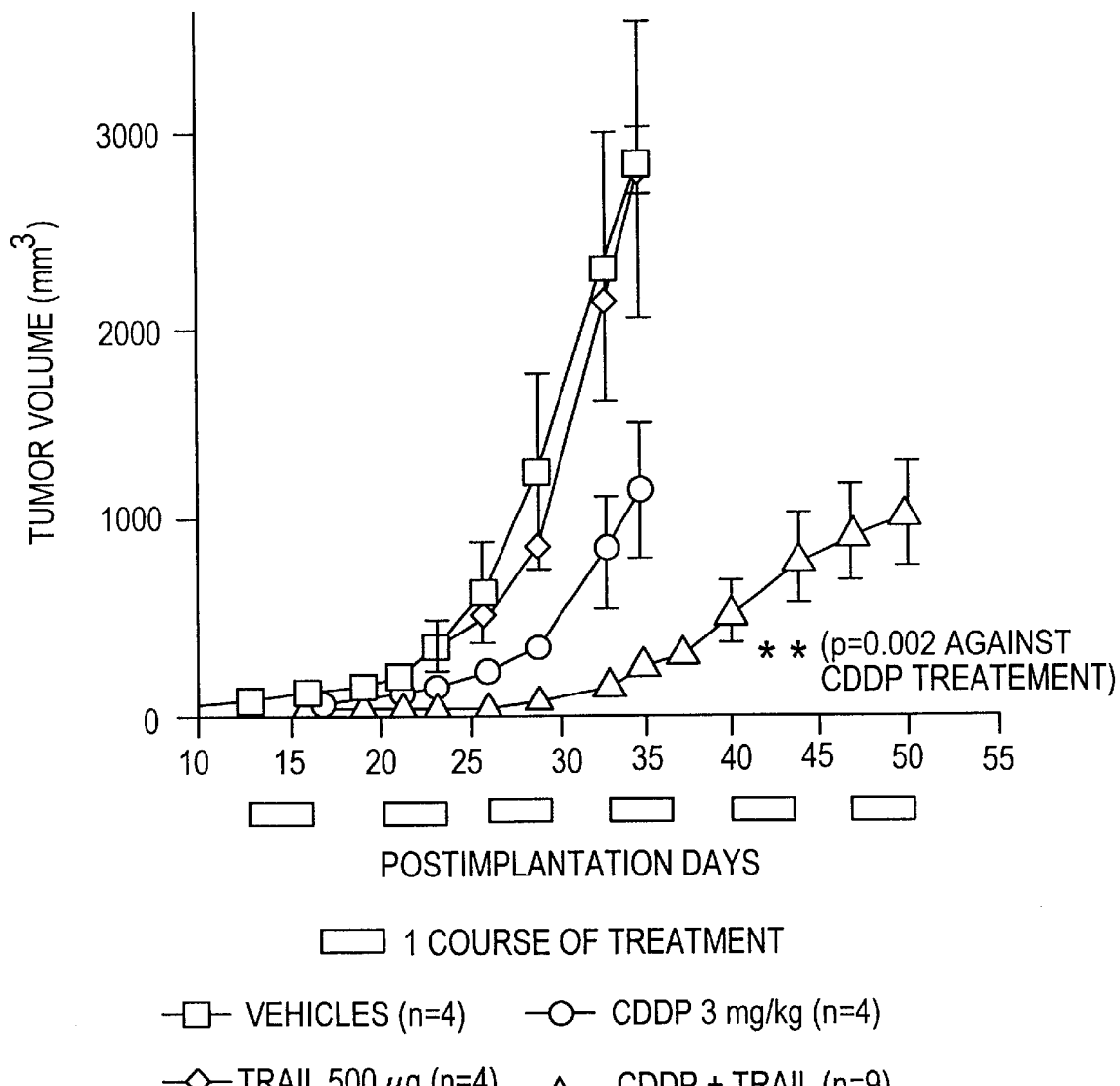
FIG. 4 demonstrates tumor regression in subject animals.

Four of the mice who received the combination therapy showed complete tumor regression, and one showed progressive regression. See FIG. 4.

EXAMPLE 9

These experiments were designed to determine the suppressive effect of the drug combination on tumor formation.

The same protocol as was employed in example 8, supra, was used, except the drug or control was administered at the start of the protocol, i.e., when the tumor cells were administered. Four animals were used in each group.

Figure 5:
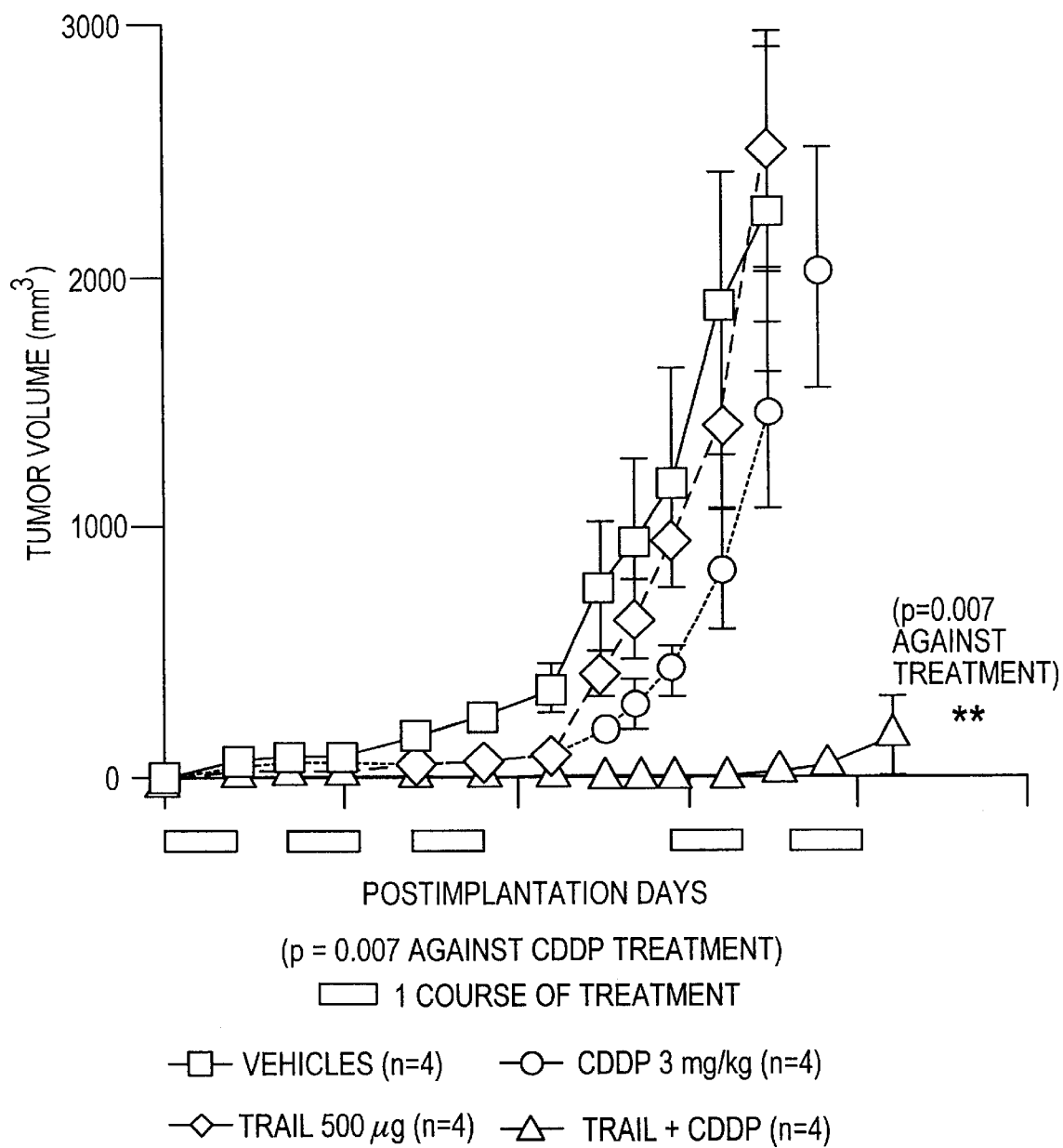
FIG. 5 presents data showing the growth suppressive effect of drug compositions of the invention.

Two of the four animals receiving combination therapy did not develop any tumors by 42 days from the start of the experiment. Further, the average tumor volume for the remaining mice was drastically lower. See FIG. 5.

EXAMPLE 10

These experiments were designed to generate survival curve information.

Figure 6:
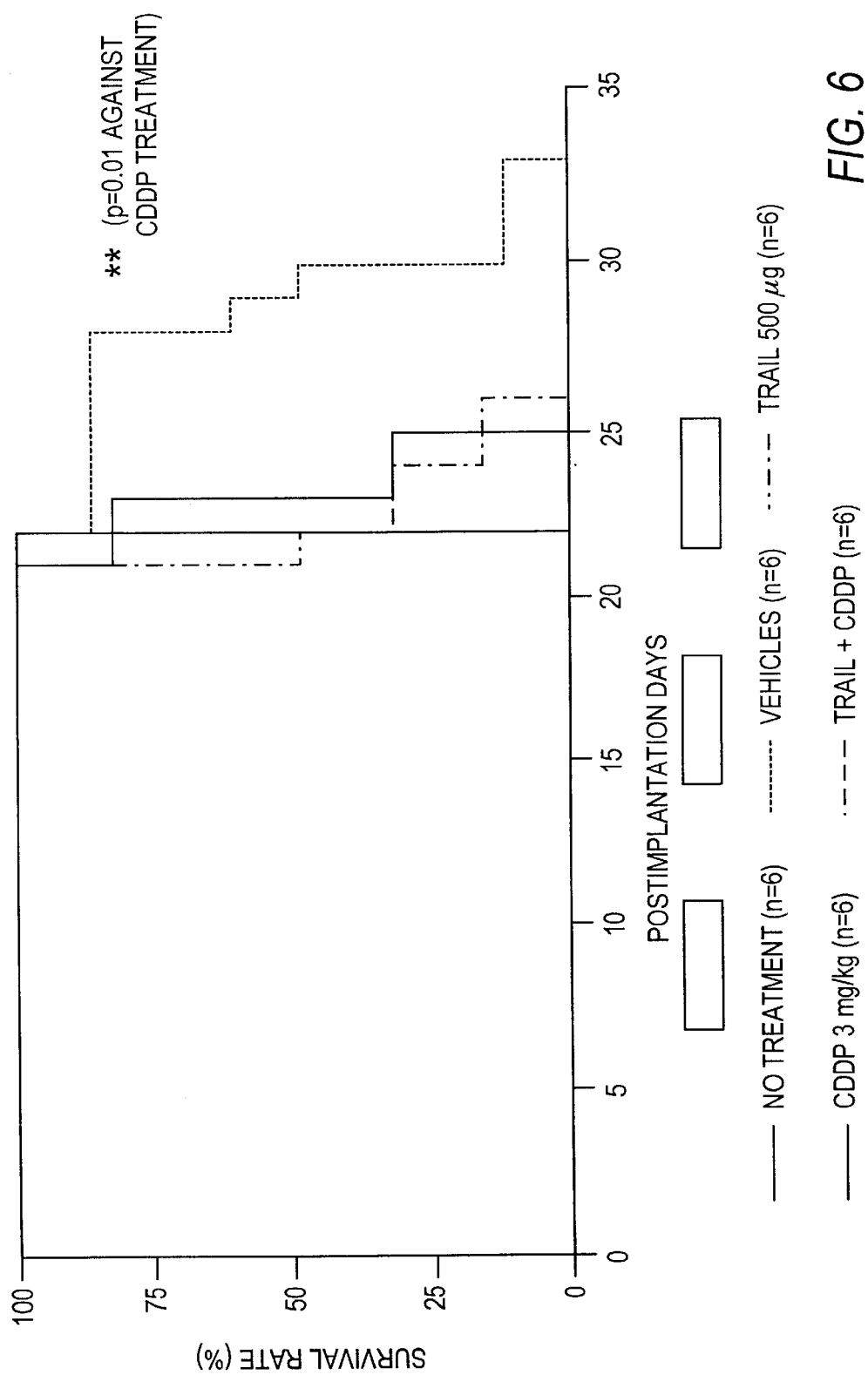
FIG. 6 displays the results obtained with intracerebral xenografts, using the compositions of the invention.

Nude mice were divided into 5 groups of six mice per group. All mice were then inoculated with $5 \times 10^5$ U87MG cells, intracerebrally. One group received no treatment whatsoever. The four remaining groups received the same treatments referred to in examples 8 and 9, for a period of 3 weeks. A survival curve was generated, and is depicted in FIG. 6. There was a 46.7% survival elongation in the group which received the combination therapy.

EXAMPLE 11

These experiments were designed to determine whether combination therapy had any toxic effect on subject animals.

In these experiments, mice did not receive any tumor innoculant. Rather, 12 mice were divided into four groups of 3 mice each, and received the treatment indicated in examples 8 and 9, supra. After 3 courses of treatment, the animals were weighed; and body weight was compared to body weight at day 0.

Figure 7:
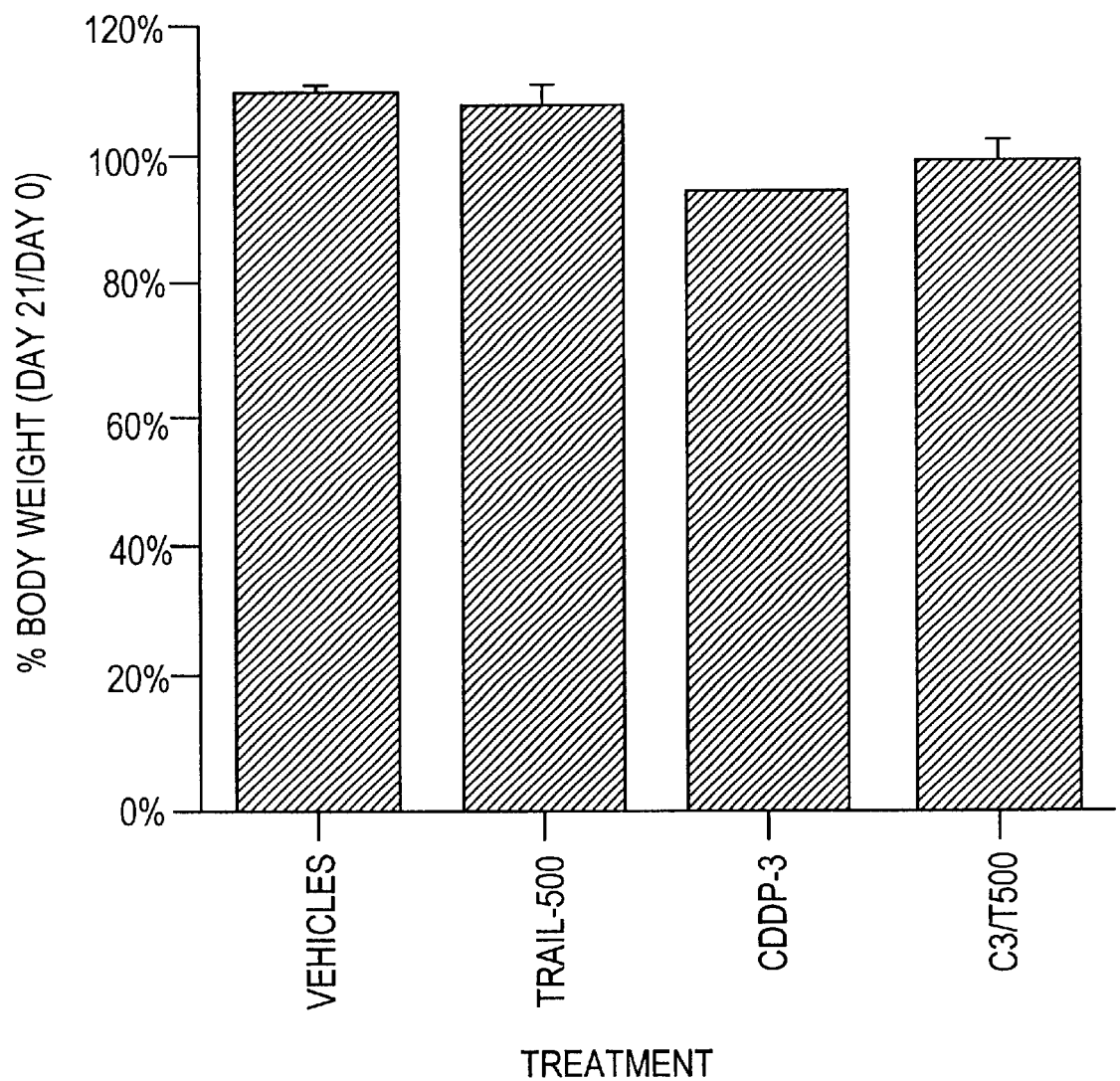
FIG. 7 displays results obtained showing lack of toxic effect of the compositions.

FIG. 7 shows that there was no apparent toxic effect on the animals.

The foregoing disclosure describes features of the invention, which include compositions useful in the treatment of conditions where it is desirable to induce cellular apoptosis. These compositions comprise both the molecule known as "TRAIL" (tumor necrosis factor related apoptosis inducing ligand), and at least one DNA damaging drugs, such as CDPP, VP16, or BCNU in amounts suitable for treating these conditions. Other therapeutic agents may be used as well, as detailed infria.

For purposes of this disclosure, "TRAIL" is intended to include any and all forms of the TRAIL molecule which bind to the DR5 receptor. Such forms of the molecule include wild type and recombinant forms of the molecule whether expressed in a eukaryotic or a prokaryote, and subject to post-translational modifications of any type, as long as these modifications do not eliminate the ability of the molecule to bind to the DR5 receptor. U.S. Pat. No. 5,763,223, referred to supra, teaches various truncated, glycosylated, unglycosylated, and soluble forms of the TRAIL molecule, demonstrating that the full length molecule is not required for receptor binding. Any such form of the molecule which binds to the DR5 receptor is thus a part of the invention. As has been shown, supra, and in the prior art, it is possible to determine whether or not a particular molecule binds to the DR5 molecule. Hence, any of the forms of the molecule which are of interest can be tested to determine if these do, in fact, retain the ability to bind DR5.

Also, a feature of the invention is the use of any DR5 ligand in combination with DNA damaging drugs described supra. Again, as the art is familiar with how to determine if a particular molecule binds to DR5, one can determine this using standard techniques, and then combine these with the therapeutic agents.

Also a part of the invention are methods for treating pathological conditions, such as neoplasias, by administering both a DR5 ligand and a DNA damaging agent to a subject in need thereof. The amount of the DR5 ligand and the DNA damaging agent may vary; however, preferred ranges in treatment protocols for humans include from about 20–300 mg/m$^2$, preferably about 40 mg/m$^2$ of BCNU administered intravenously, per day, from about 15 to about 45 mg/m$^2$, preferably about 30 mg/m$^2$ of CDDP administered intravenously per day, and from about 25 to about 100 mg of VP16, preferably about 50 mg, per day, administered orally. The '223 patent which has been incorporated by reference is referred to herein for information on dosages of the TRAIL molecule and derivatives thereof. The materials may be administered intravenously, intraperitoneally, subcutaneously, orally, in slow release form, infusion, etc., as any standard pharmacological mode of delivery will work. The two agents may be administered via the same route, or different routes may be used. Further, the agents may be combined in a "one pot" formulation, or may be administered sequentially. To this end, the composition of the invention may include one pot formulations, or kit type formulations where a separate portion of each drug is provided in a container means, such that the drugs can be administered sequentially. As indicated supra, the compositions preferably comprise a TRAIL molecule, and one or more DNA damaging drug such as BCNU, VP16, or CDPP. The therapeutic methods may include administration of other therapeutic agents, and the composition may include additional components as well.

The efficacy on glioma suggests efficacy in those conditions where an abnormality is characterized, inter alia, by rapid cell turnover. Neoplasias such as gliomas are but one example of such conditions. Others include benign neoplasms, and non-neoplastic conditions involving, e.g., proliferative lesions. Exemplary of such conditions are colon disorders such as Crohn's disease, polyposis coli, ulcerative colon disorders, and so forth.

The methodology described herein should also be seen as an adjunctive therapy to other therapeutic regimes, such as radiotherapy, treatment with antibodies, and other traditional forms of anticancer therapies.

Other features of the invention will be clear to the skilled artisan, and need not be reiterated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Composition useful in treating a condition, comprising (i) a TRAIL molecule and (ii) a DNA damaging agent sufficient to affect apoptosis.

2. The composition of claim 1, wherein said DNA damaging agent is BCNU, CDPP or VP16.

3. The composition of claim 1, wherein (i) and (ii) are separated from each other.

4. The composition of claim 2, wherein (ii) is present at from about 20–300 mg/m$^2$.

5. A method for treating a subject with a condition that requires affecting apoptosis, comprising administering an amount of the composition of claim 1 to said subject sufficient to affect apoptosis.

6. The method of claim 1, wherein said condition is cancer.

7. The method of claim 6, wherein said cancer is glioma.

8. The method of claim 5, wherein said DNA damaging drug is BCNU, CDDP, or VP16.

9. The method of claim 6, comprising administering said composition intravenously, intraperitoneally, or orally.

* * * * *